United States Patent [19]
Maynard

[11] Patent Number: 5,816,247
[45] Date of Patent: Oct. 6, 1998

[54] MONITORING AN EEG

[75] Inventor: Douglas E. Maynard, Blackboys, United Kingdom

[73] Assignee: RDM Consultants Ltd., United Kingdom

[21] Appl. No.: 663,385

[22] Filed: Jun. 13, 1996

[30] Foreign Application Priority Data

Jun. 13, 1995 [GB] United Kingdom .................... 9511964

[51] Int. Cl.⁶ ....................................................... A61B 5/04
[52] U.S. Cl. .............................. 128/731; 128/732; 395/21
[58] Field of Search ..................................... 128/731, 734; 395/21

[56] References Cited

U.S. PATENT DOCUMENTS

| | | |
|---|---|---|
| 4,214,591 | 7/1980 | Sato et al. . |
| 4,279,258 | 7/1981 | John . |
| 4,412,547 | 11/1983 | Callahan et al. . |
| 4,846,190 | 7/1989 | John . |
| 5,083,571 | 1/1992 | Prichep . |
| 5,092,343 | 3/1992 | Spitzer et al. ........................... 128/702 |
| 5,195,530 | 3/1993 | Shindel . |
| 5,230,346 | 7/1993 | Leuchter et al. . |
| 5,269,302 | 12/1993 | Swartz et al. . |
| 5,299,118 | 3/1994 | Martens et al. . |
| 5,311,876 | 5/1994 | Olsen et al. . |
| 5,320,109 | 6/1994 | Chamoun et al. . |
| 5,325,862 | 7/1994 | Lewis et al. ............................. 128/731 |
| 5,335,657 | 8/1994 | Terry, Jr. et al. . |
| 5,349,962 | 9/1994 | Lockard et al. . |
| 5,357,976 | 10/1994 | Feng . |
| 5,392,788 | 2/1995 | Hudspeth . |
| 5,417,211 | 5/1995 | Abraham-Fuchs et al. ......... 128/653.1 |
| 5,533,511 | 7/1996 | Kaspari et al. .......................... 128/672 |
| 5,584,291 | 12/1996 | Vapola et al. ........................... 125/630 |

FOREIGN PATENT DOCUMENTS

| | | |
|---|---|---|
| 1169494 | 6/1984 | Canada . |
| 0355506 | 8/1989 | European Pat. Off. . |
| 0437012 | 1/1990 | European Pat. Off. . |
| 0137705 | 4/1990 | European Pat. Off. . |
| 0150125 | 9/1990 | European Pat. Off. . |

(List continued on next page.)

OTHER PUBLICATIONS

The Self–Organizing Map, T. Kohonen, Proceedings of the IEEE, vol. 78, No. 9, Sep. 1990, 1464–1480.

E.E.G. Monitoring for the Control of Anaesthesia Produced by the Infusion of Althesin in Primates, P.F. Prior, D.E. Maynard, J.B. Brierley, British Journal of Anaesthesia, 1978, 50, pp. 993–1001.

Development of the CFM: The Cerebral Functional Analysing Monitor (CFAM), D.E. Maynard, Annales De Le Anesthésiologie Francaise, vol. XX, No. 3, 1979, pp. 253–255.

EEG Processing by the Cerebral Function Monitor (CFM), D.E. Maynard, Annales De Le Anesthésiologie Francaise, vol. XX, No. 3, pp. 170–174.

Use of Neural Network Analysis to Classify EEG Patterns Against Depth of Midazolam Sedation in Intensive Care Unit Patients, R.A. Veselis, R. Reinsel, S. Sommer & Graziano Carlon, Journal of Clinical Monitoring, vol. 7, No. 3, Jul. 1991, pp. 259–267.

Self–Organizing Map in Recognition of Topographic Patterns of EEG Spectra, S–L. Jotsiniemi, S. Kaski, T.A. Larsen, IEEE Transactions on Biomedical Engineering, vol. 42, No. 11, Nov. 1995, pp. 1062–1068.

CFAM2–1–2 Channel Brain Monitor, 2 Page Pamphlet by RDM Consultants Limited.

*Primary Examiner*—Jennifer Bahr
*Assistant Examiner*—David M. Ruddy
*Attorney, Agent, or Firm*—Oppenheimer Poms Smith

[57] ABSTRACT

An apparatus and method for EEG monitoring provides multi-dimensional classification of EEG samples, using a neural network having multiple outputs trained upon a training set of samples to define an n-dimensional space in which to classify the samples and provide to the user a display of that space.

16 Claims, 14 Drawing Sheets

FOREIGN PATENT DOCUMENTS

| | | |
|---|---|---|
| 4689999 | 10/1990 | European Pat. Off. . |
| 0638193 | 10/1993 | European Pat. Off. . |
| 1247491 | 9/1971 | United Kingdom . |
| 1247492 | 9/1971 | United Kingdom . |
| 1335219 | 10/1973 | United Kingdom . |
| 2016708 | 9/1979 | United Kingdom . |
| WO9103979 | 4/1991 | WIPO ............................... 128/204.21 |

TITLE
\cfam2\NEO1\nn\COMBINE3.z12
Computation date: 15:Feb:1995 time: 09:42
Class menu for training on three axis coordinates
A coordinate of 000 = omit this class on this axis
<- exit     Select item to alter->
Axes        X   Y   Z   <total items in category
DATA
XA2829W    030,050,000,<0064>,active sleep well 28-29weeks
XA3031W    040,050,000,<0114>,active sleep well 30-31weeks
XA3233W    050,050,000,<0093>,active sleep well 32-33weeks
XA3435W    060,050,000,<0162>,active sleep well 34-35weeks
XA3637W    070,050,000,<0070>,active sleep well 36-37weeks
XA3839W    080,050,000,<0080>,active sleep well 38-39weeks
XA4041W    090,050,000,<0044>,active sleep well 40-41weeks
XA4243W    100,050,000,<0031>,active sleep well 42-43weeks
XA44xxW    110,050,000,<0000>,active sleep well >= 44weeks
XBxx31W    040,040,000,<0054>,quiet sleep well <= 31weeks
XB3233W    050,040,000,<0036>,quiet sleep well 32-33weeks

Figure 11

TITLE
\cfam2\NEO1\nn\COMBINE3.v12
Computation date: 15:Feb:1995 time: 09:42
Variables to be included in training set
0=exclude    1=include
<- exit          toggle on-off ->
DATA
CHANNELS    chan1 only
MEANS___1, means of all variables
SDs_____ 1, standard deviations of all variables
SKEWS___1, skews of all variables
KURTOSIS1, kurtoses of all variables
Lmin____ 0, minimum line interference
Lmax____ 0, maximum line interference
Zmin____ 0, minimum source impedance
Zmax____ 0, maximum source impedance
Mmin____ 1, minimum muscle amplitude
Mmax____ 1, maximum muscle amplitude
Amin____ 1, minimum of amplitude distribution
etc.

Figure 12

TITLE
\cfam2\NEO1\nn\COMBINE3.y12
Computation date: 15:Feb:1995 time: 09:42
Control of network type to be trained <- exit     select to modify ->
DATA
NNET_B   one classifier per axis
INPUTS   080, total input variables
HIDLAY1  025, first hidden layer
HIDLAY2  025, second hidden layer
OUTLAY   02, output layer
AXIS     XY,train both axes together
T_RANGE  05, range in which o/p correct

Figure 13

| | |
|---|---|
| XYINCL  15,25 | YLABEL  State |
| XYINCL  15,35 | LTX     20,27 |
| XYINCL  35,35 | LTX     30,29 |
| XYINCL  35,35 | LTX     40,31 |
| XYINCL  25,45 | LTX     50,33 |
| XYINCL  25,55 | LTX     60,35 |
| XYINCL  35,55 | LTX     70,37 |
| XYINCL  35,65 | LTX     80,39 |
| XYINCL  45,65 | LTX     90,41 |
| XYINCL  45,85 | LTX     100,43 |
| XYINCL  105,85 | LTY    30,TA |
| XYINCL  105,35 | LTY    40,QSleep |
| XYINCL  65,35 | LTY     50,ASleep |
| XYINCL  65,25 | LTY     60,Quiet |
| DISPLAYS 1,XY | LTY     70,Handled |
| XMIN    10 | LTY     80,Crying |
| XMAX    110 | |
| YMIN    20 | |
| YMAX    90 | |
| XLABEL  Weeks | |

Figure 14

MONITORING AN EEG

BACKGROUND OF THE INVENTION

This invention relates to the field of monitoring and measuring an EEG (electroencephalogram).

In the prior art, an EEG is recorded from a number of pairs of scalp electrodes and processed according to, for example, the software available on a system known as the CFAM2 (Cerebral Function Analysing Monitor 2) made by RDM Consultants Ltd. from 1989 onwards. An earlier system known as CFAM1, although obtaining the same data as the later CFAM2, did so using a different computational method. The CFAM2 hardware and software acquires both processed and unprocessed EEG data and records it on a hard disc. Later the records may be replayed and statistics of the on-line measures made on suitable record sections placed into categories predefined by the user of the machine. Over many records these form a database of statistical measures on data in the defined categories. The CFAM2 software enables new categories to be defined and data transferred to them as appropriate. It enables a number of statistical tests to be made on the data in each category to give an indication of the homogeneity of the data in each category and so assist the user in identifying statistical outliers and miscategorised data.

SUMMARY OF THE INVENTION

An object of the present invention is to enable data classification and its presentation to the user to be improved.

According to one aspect of the invention, there is provided apparatus for electroencephalographic (EEG) patient monitoring, the apparatus comprising:

input circuitry for receiving from a plurality of electrodes attached to sectors of patients' heads, signals representative of patients' brain waves, the input means inluding amplifier means and signal processing means for amplitude and spectral analysis of the signals to provide for each of a plurality of segments of the signals a set of signals representative of a plurality of amplitude and frequency properties of the brain waves;

means for applying statistical processing to the set of signals to derive therefrom a set of values representative of the brain waves in the associated signal segment;

input means for defining for each of a plurality of said patient events n (where n at least equal to 2) classifying values so that each event is categorised by n values;

neural network means having a training mode (for deriving from a plurality of said sets of values and from the associated defined classifying values output classifying values representative of patient conditions) and a classifying mode (for deriving from one of said sets of values n output classifying values obtained from the neural network means as conditioned by training in the training mode);

display means for displaying in n-dimensional form the output classifying values of the neural network means; and memory means for storing data values obtained from the input circuitry.

According to another aspect of the invention, there is provided a system for incorporating neural network based analysis of EEG data to generate scaled information of a patient measure such as increasing severity of a diagnostic category or a scale of level of awareness, where more than one such scale may be combined to produce a multidimensional graphical display of such scales or the variation of such scaled information with time.

According to another aspect of the invention, an EEG is acquired from a number of pairs of scalp electrodes and processed according to, for example, the software available on the system known as the CFAM2 or CFAM3; the results of this processing are further operated on by a neural network.

According to yet another aspect the invention provides a method of determining EEG categories of patients, the method comprising:

obtaining a plurality of sets of training data from EEG records of a plurality of patients;

determining categories for classifying said sets, each category being defined by n (where n is an integer >1) classifying items;

defining an n-dimensional space in which said determined categories are represented as distinct coordinates;

training a neural network with n outputs, utilising said plurality of sets as input data and said defined categories as target outputs; and applying a set of EEG data from a patient to the neural network to derive therefrom a position in said space, whereby a patient category can be assessed.

Such a method may obtain training data by:

making EEG measurements upon a plurality of patients to obtain respective patient records;

obtaining for each of a plurality of sections of said records a first set of values representing the statistical relationship between amplitude values of said records;

dividing each such section into bands of different frequency ranges;

obtaining from those ranges for each section a second set of values representing the statistical relationship between magnitudes in each band over the associated section; and said sets of training data comprise combinations of the first and second sets of values. As for the previous CFAM2 hardware and software system, the present invention may also acquire both processed and unprocessed EEG data and record it on a hard disc. Later the records may be replayed and statistics of the on-line measures made on suitable record sections placed into categories predefined by the user of the machine. Over many records these form a database of statistical measures on data in the defined categories. The software enables new categories to be defined and data transferred to them as appropriate. It enables a number of statistical tests to be made on the data in each category to give an indication of the homogeneity of the data in each category and so assist the user in identifying statistical outliers and miscategorised data.

For a better understanding of the invention, and to show how the same may be carried into effect, reference will now be made, by way of example, to the accompanying drawings.

BRIEF DESCRIPTION OF THE DRAWINGS

FIGS. 11 to 14 show specifications for the input to, design of a neural network structure and the format of the output display;

DETAILED DESCRIPTION OF EMBODIMENTS
TERMINOLOGY s.s.=samples per second.

uV=microvolts.

pkpk=peak to peak.

rms=root mean square.

kohms=kilo ohms.

s&c=sine and cosine filters.

A preferred embodiment will now be described, being based in some respects upon a prototype system called CFAM3; alternative embodiments could be based upon an earlier system known as CFAM2 and mentioned above. Two prototype CFAM3 systems called CFAM3b (b=basic) were installed in a hospital in Sheffield, England in March 1995 and their input hardware is similar to that of the present embodiment, but they did not record values. They provided amplitude and frequency distributions on a paper trace. A version CFAM3a (a=archive) was delivered in March 1996 with hard disc for recording data and retrospective statistical analysis. As will become apparent, the preferred embodiment now to be described differs in various respects, as will be described.

Figure 1:
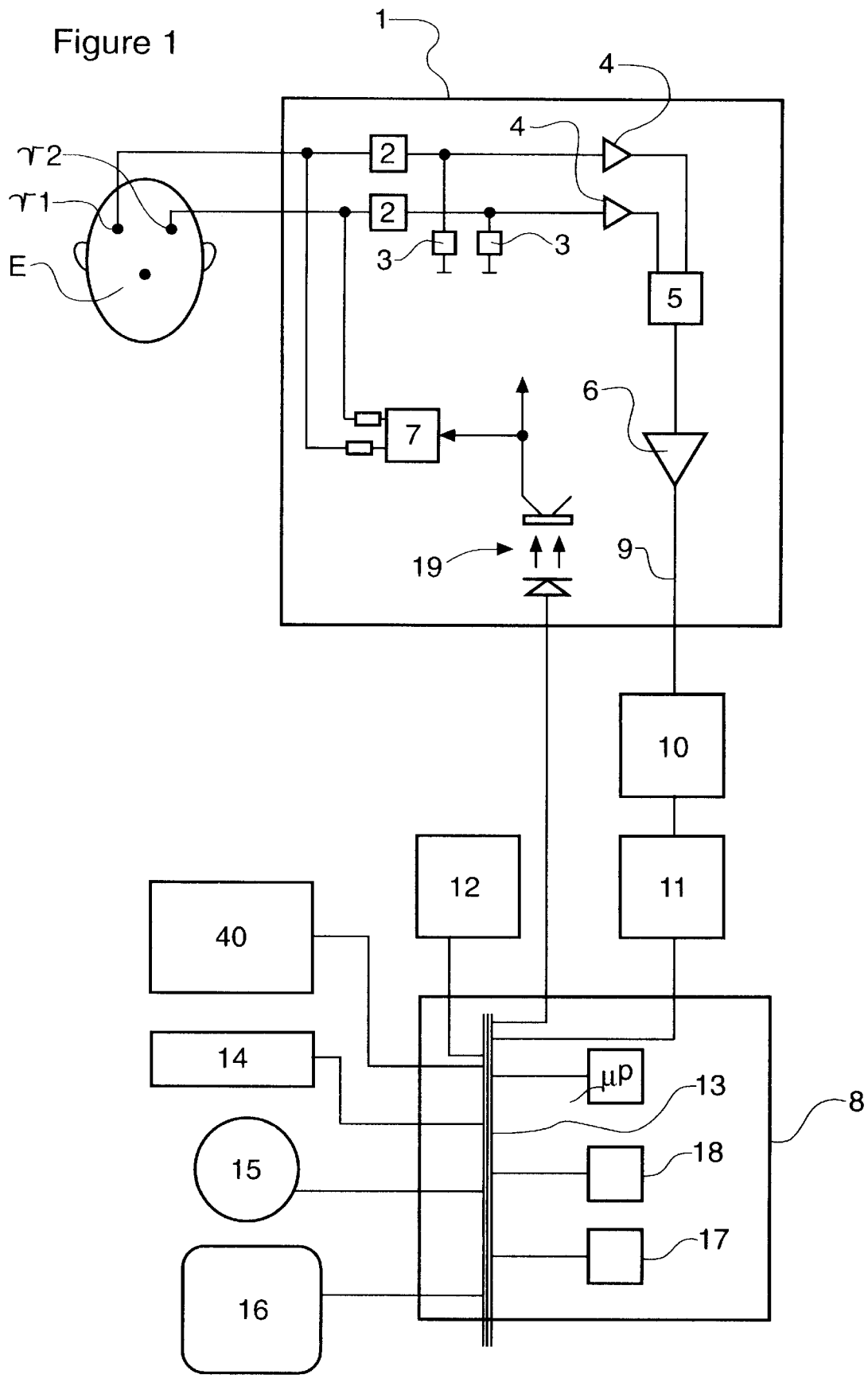
FIG. 1 is a block diagram of brain monitor equipment.

The hardware and signal processing paths of the preferred embodiment will now be described with reference to FIG. 1 to enable a proper understanding of the advance made by this invention.

Hardware of the brain monitor

There are provided a number of recording channels for recording EEG from scalp electrodes of a patient, these channels being connected to a header amplifier circuit 1, which may be in accordance with the CFAM3 apparatus. For illustration purposes FIG. 1 shows a single channel. According to the application 1, 2, 3 or 4 electrode pairs (e.g. r1, r2) may be used plus a reference electrode (E) connected to the input circuit ground of the header amplifier circuit to minimise common mode interference. In the header amplifier circuit, before amplification, there are low pass filter circuits 2 to reduce radio-frequency interference in the input signal, plus voltage limiting devices 3, such as gas discharge tubes and limiting or zener diodes, to protect following amplifiers 4 from high voltage discharges such those produced by a defibrillator.

The EEG signal is then amplified by the amplifiers 4, retaining a DC component. The signal is then presented to a high pass limiting circuit 5, time constant typically 0.3 second, which removes the DC component but which, should the DC component be above a given level, or the DC plus remaining AC signal be above that level, will cause subsequent amplifier stages 6 to be forced into overload, indicating an artefactual signal.

Additionally a current source 7 of a sine wave at 277 Hz feeds across electrode pairs for use in measuring electrode impedance This signal may be turned off by command of a main data processor 8 if required, that command being sent on a control path via opto-isolator 19; the control line may convey other control signals, e.g. to short-circuit the inputs of unused amplifiers 4. The impedance signal is amplified along with the EEG signals and removed later by filtering.

Patient isolation is provided by means of Burr-Brown ISO121 medical grade amplifiers 6. The above circuitry is contained in a header amplifier box which is connected to the main instrument by means of a multicore cable 9. The main instrument provides calibration sources, on the front panel for the CFAM2, and in a header amplifier docking/transport port for the CFAM3, by means of which the characteristics of the isolated patient amplifiers and subsequent hardware may be checked against references.

Internally to the CFAM2/CFAM3 equipment the signal is sampled at 9600 samples per second. For the CFAM2 apparatus there is an anti-alias filter in each channel to provide >90 dB attenuation above 4,800 Hz followed by sample and hold and 16 bit analog to digital conversion by a successive approximation amplifier. In the present embodiment and as is in the CFAM3a and b apparatus, this is replaced by a circuit 10 which comprises an anti-alias filter with a slower rate of attenuation, and no sample and hold, and a 16 bit sigma-delta analog to digital converter with inbuilt digital low pass filtering to give a 9600 samples per second output data rate per channel.

Figure 2:
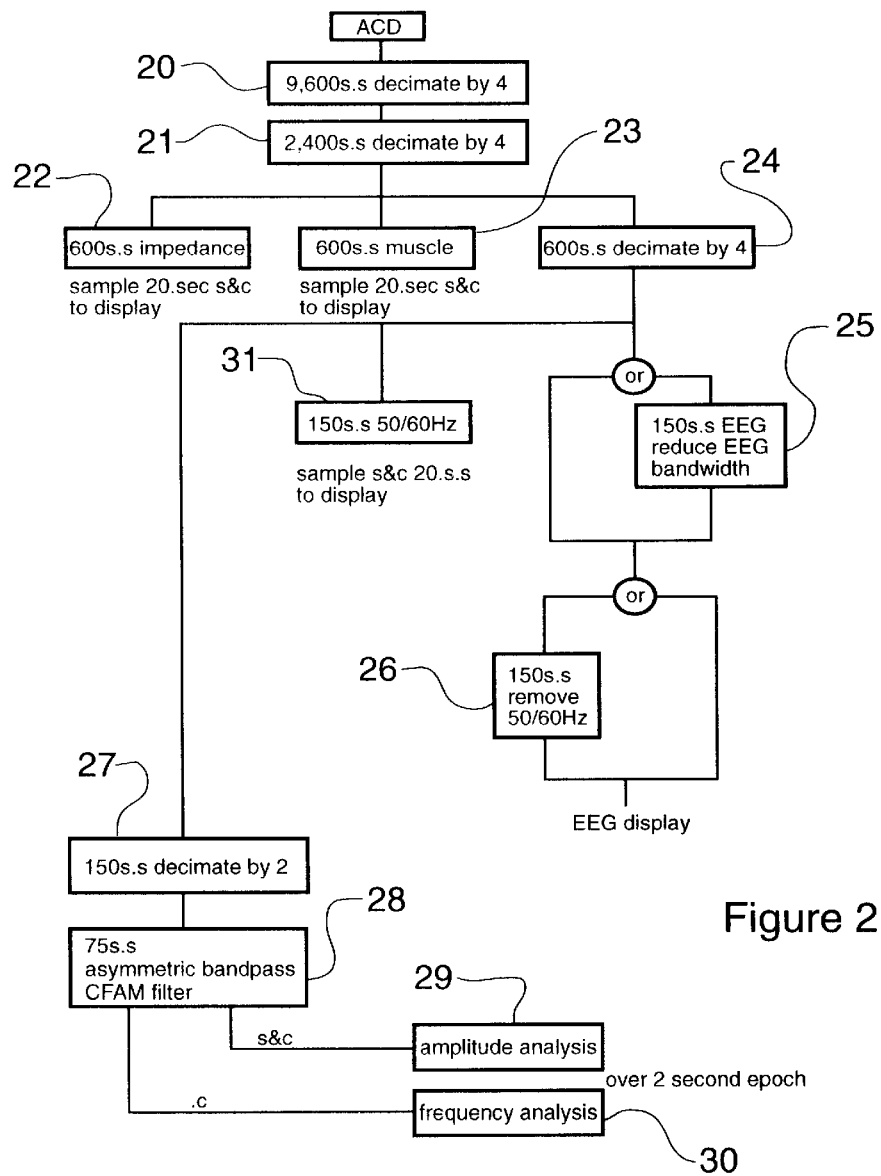
FIG. 2 is a block diagram illustrating a digital filtering process.

The analog to digital convertor data is read by a Motorola digital signal processor board 11 (with processor (s) of type DSP56001/2—in one example it contains two DSP56002 processors) which is programmed to digitally filter the signals in stages as given by the filter tree in FIG. 2.

In the preferred embodiment, the hardware can be expanded with an extra board 12 containing extra DSPs and/or special function neural logic chips to boost the computational performance. No such extra board or neural logic or neural software exists in CFAM3a or b. The board links to the DSP board 11 and is powered from and can also be addressed from the main computer bus 13. Also attached to this bus are a keyboard 14, mass storage 15 and visual display 16. The main data processor includes, as usual, RAM and ROM memory 17 and 18 coupled to the bus. A thermal printer 40 is attached to the bus 13 to give a print of screen displays. This enables an observer to see at a glance a recording of the output over the past few hours and provides a chart for the patient's clinical notes.

Filter tree

The signal is digitised at a high rate to enable evoked potentials to be computed but this is not part of this description. (For these the second DSP processor may be used to accumulate, average and process potentials generated by external auditory, galvanic or photic stimuli or any other suitable stimulus).

The 9600 s.s signal delivered by the analog to digital convertor in circuit 10 is processed by filtering software in the DSP board 11, the flow chart of that software being given in FIG. 2. This software and the remainder described below are in this embodiment written in the C or C++ language.

At 20 and 21 the signal is decimated twice to produce a 600 s.s. signal.

A filter 22 tuned to the impedance monitoring frequency and having sine and cosine parts samples the 600 s.s. signal at 20 times per second to produce rms measurements of the electrode impedances. These measurements are transferred to the storage 15 and display of the main computer.

A filter 23 with multiple pass and stop bands is used to select frequencies at which scalp muscle activity may occur, uncorrupted by mains frequencies (50/60 Hz) and their harmonics, the impedance signal, or EEG signals. This has sine and cosine outputs and is used to sample the 600 s.s. signal 20 times per second to produce rms measurements of muscle activity. These measurements are supplied to storage 15 and the display of the main computer.

The 600 s.s. signal is then decimated at step 24 by 4 to 150 s.s. to form the basic EEG signal before further processing. The EEG to be displayed, and stored on the hard disc, may be further low pass filtered at 25 (without decimation) if desired and the mains (50/60 Hz) frequency may also be filtered out at 26 if required.

Figure 3:
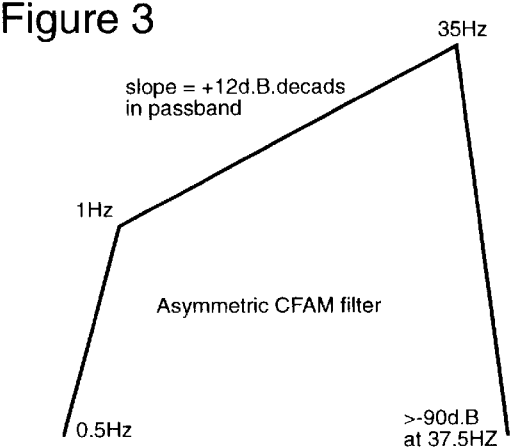
FIG. 3 shows a band pass filter response.

A further branch 27 of the filter tree decimates the signal to 75 s.s. then passes it to an asymmetric band pass filter 28 having a frequency response as in FIG. 3. This filter shape is closely similar to that used in the original CFM brain monitor (1968) and later CFAM1 monitor (1975).

Data output from the asymmetric filter 28 at 75 samples per second are subjected to amplitude and frequency analysis at 29 and 30 in successive two second epochs.

Filter branch 31 filters the mains frequency (50/60 Hz) having sine and cosine parts which is used at 20 times a second to measure the amplitude of any mains interference. The data is passed to the display and is recorded on the hard disc with the other data.

Amplitude analysis

Sine and cosine outputs from the asymmetric filter 28 are combined (as SQRT(s*s+c*c) ) to provide an asymmetrically filtered EEG signal modulation envelope. Over two seconds 150 such measures are each first subjected to a logarithmic conversion to convert from a Rayleigh to a near Gaussian amplitude distribution. Statistical routines are then applied to the measures so that they are ranked in order of magnitude and the minimum, 10th centile, mean, 90th centile and maximum values of the amplitude distribution are recorded, these values being referred to herein as Amin, A10, Amean, A90 and Amax. When the record is replayed, there is a routine which calculates for use in classifying the data two further values: Awide (=A90-A10—a measure of the width of the amplitude distribution) is also recorded, as is Asym which is a measure of the asymmetry of the amplitude distribution and which is calculated as (A90-Amean)/(A90-A10).

Frequency Analysis

This takes only the cosine asymmetric output of the filter 28. The last 32 samples from the previous epoch are tapered up from zero and added to the front of the 150 samples in the present epoch, making 182 samples. The last 32 samples of the present epoch are tapered to zero and then extended by zeroes to make a sample length of 256. This is input to a 256 point Fast Fourier Transform the output of which inherently provides sine and cosine measures in 0.5 Hz frequency bands up to 37.5 Hz. These are then combined by means of root mean square summation within each EEG frequency band, these being for this purpose defined as: VLP <0.9 Hz, Delta 0.9 to 3.5 Hz, Theta 3.5 to 8.5 Hz, Alpha 8.5 to 12.9 Hz, Beta >12.9 Hz.

A bandwidth correction is applied such that, should the frequency spectrum of the EEG signal have been attenuated at −12 dB per decade over the range measured, the output in each frequency range will be the same. A further computation is also made to calculate the percentage of the total rms EEG (bandwidth corrected) activity occurring in each frequency band, i.e. %VLF, %Delta and so forth.

In each 2 second epoch the following outputs are obtained for each channel:
Epoch start-time
Overload status—(causes ADC to indicate+ or − full scale— this is detected and a status flag is set in software to indicate if data is valid)
Muscle $\mu$V maximum in epoch (Muscle_max)
Muscle $\mu$V minimum in epoch (Muscle_min)
Line frequency $\mu$V maximum (Line_min)
Line frequency $\mu$V minimum (Line_max)
Electrode impedance ohms maximum (Kohms_max)
Electrode impedance ohms minimum (Kohms_min)
(the Muscle, Line frequency and impedance are monitored in the filter tree and the max and min values in any 2 second epoch are sent to processor 8)
Minimum log amplitude (Amin)
10th centile log amplitude (A10)
90th centile log amplitude (A90)
Maximum log amplitude (Amax)
Mean log amplitude (Amean)
Percent time signal below $1\mu$V (Suppr)
Bandwidth corrected $\mu$V in VLF band (VLF)
Bandwidth corrected $\mu$V in delta band (Delta)
Bandwidth corrected $\mu$V in theta band (Theta)
Bandwidth corrected $\mu$V in alpha band (Alpha)
Bandwidth corrected $\mu$V in beta band (Beta)
Percent VLF (%VLF)
Percent Delta (%Delta)
Percent Theta (%Theta)
Percent Alpha (%Alpha)
Percent Beta (%Beta)

These data, plus the filtered EEG data at 150 samples per second, are transferred to the hard disc for later replay, and to a visual display unit 16 for immediate inspection. The appearance of this display is, apart from 'button' controls, closely similar to that shown on data replay and so will be described in relation to replay and allocation to categories below.

Figure 4:
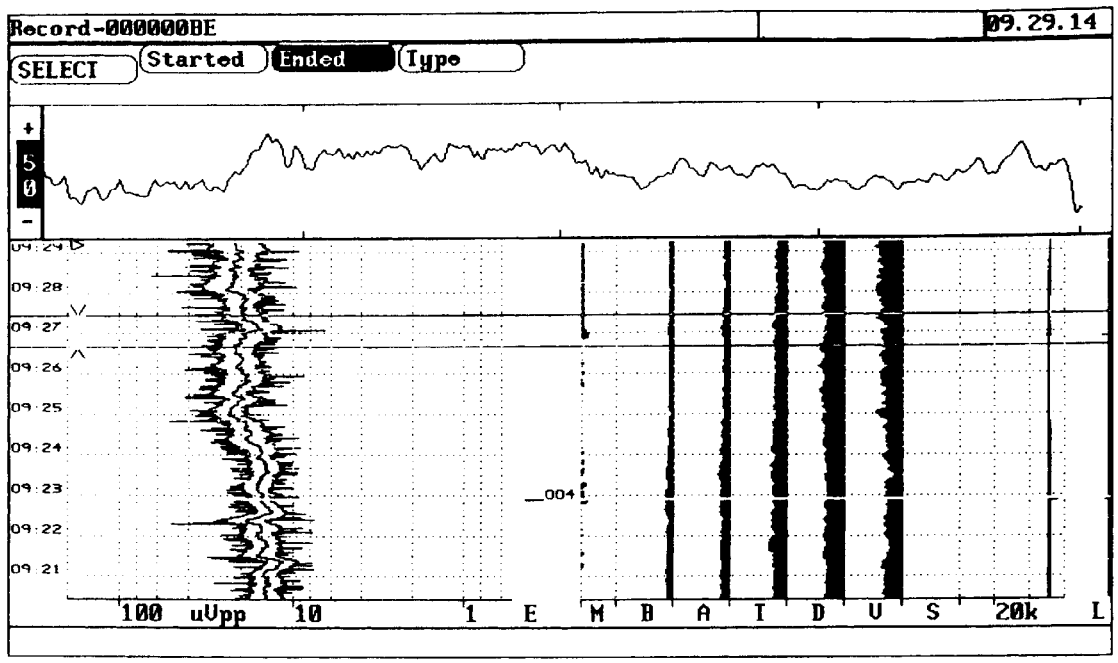
FIG. 4 shows a data display.

Both processed and unprocessed EEGs may be replayed on a visual display unit with the appearance of FIG. 4, that for a recording differing only in the button controls at the top of the display.

The date and time of the recording are given at the top right hand side. The recorded multi-channel EEG is displayed in 4 second sections, here for one channel only, and may have its vertical scale adjusted. The lower part of the display is divided into amplitude and frequency distributions.

Amplitude (on the left)

A time scale in hours and minutes is shown written up the left hand axis. The amplitude plot is on a logarithmic scale and can write up to 400 $\mu$V pkpk. The 10th centile (A10), the mean (Amean) and the 90th centile (A90) measurements (taken every 2 seconds) are displayed and have been backwards weighted in time to smooth out short term fluctuations. Amplitude excursions below the 10th centile and above the 90th centile are written in full every 2 seconds.

Markers (in the middle)

Event markers are written between the amplitude and frequency traces and numbered consecutively.

Frequency (on the right)

These traces are all constrained between adjacent time axis graticule lines. Muscle labelled M on the axis writes from left to right a continuous line up to a maximum shown of 50 $\mu$V pkpk. %Beta (B), %Alpha (A), %Theta (T), % Delta (D) and %VLF (V) write from right to left. The distance between the graticule lines represents 100%. Percent time suppression (S), written from right to left, is the percentage of time in each 2 second epoch that the signal pkpk value is below 1 $\mu$V The muscle and frequency plots and the percent time suppression plot are backwards smoothed in time.

Electrode Impedance (far right)

This is measured up to a maximum of 30 kohms, writing from right to left. A line is written between the minimum and maximum impedances measured every 2 seconds.

Mains interference (far right)

The level of 50/60 Hz interference (L) measured in $\mu$V pkpk, up to a maximum of 100 $\mu$V is written from the extreme right, up to the 0 kohms baseline.

Data selection

Figure 7A:
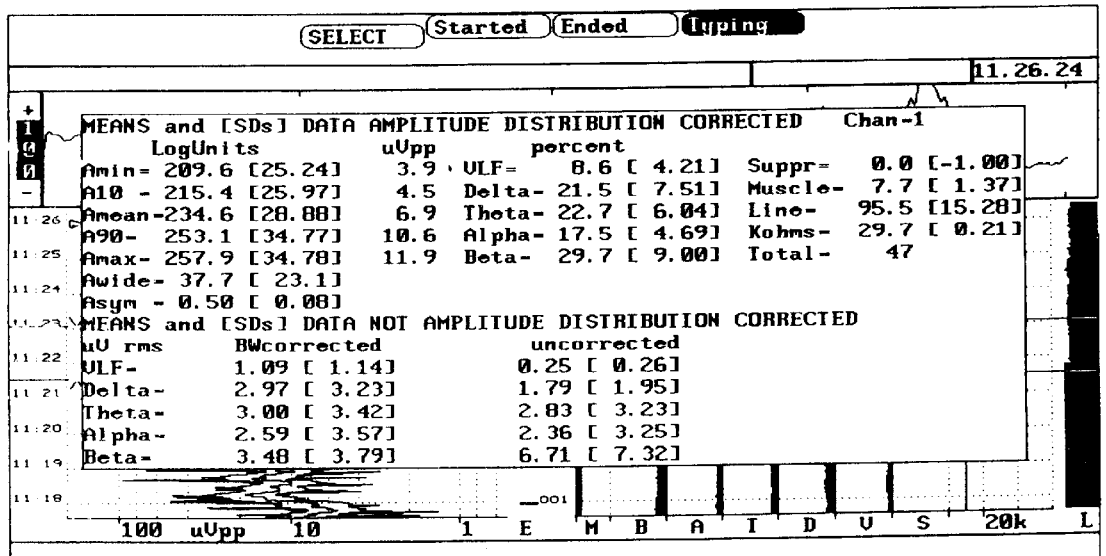
FIGS. 7a and 7b show a display of statistical data.
Figure 7B:
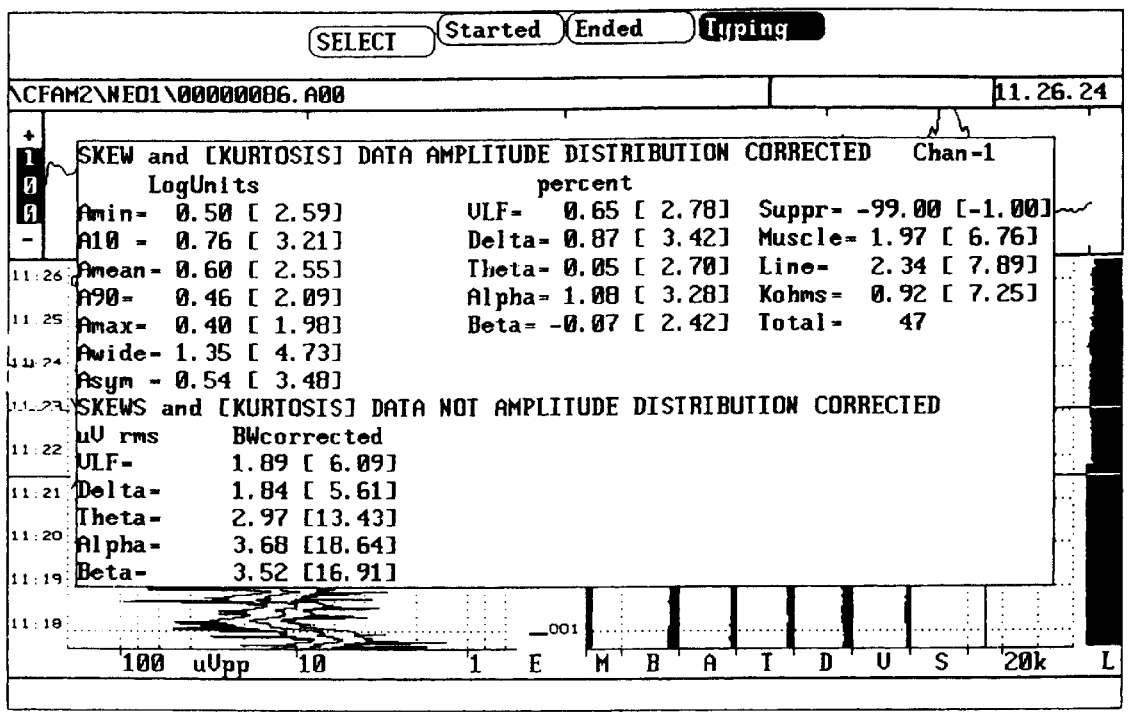

Still referring to FIG. 4, by means of 'button' operated cursors a time section of the replayed record may be bracketed and the statistics of the processed EEG measures over that time calculated. Statistical software routines for producing means, standard deviations, skews and kurtosis also generates two boxes or windows on screen which are as shown in FIG. 7a and 7b. For each measure, mean, variance, skew and kurtosis are computed. In FIG. 7a the means and standard deviations (the latter in square brackets) are shown for a section of the record comprising 47 successive 2 second epochs (Total=47 on the figure. In the first two columns are shown in Log units the means and [standard deviations] of the amplitude distribution measures. In the next column headed uVpp there are the corresponging microvolts peak-to-peak values. The relationship is Amplitude ($\mu$Vpp)=($\frac{1}{32}$)antilog$_{10}$(log value/100) where amplitude statistics are computed, they are computed from the distribution of log units.

In the columns headed percent are the means and [standard deviations] of the percentage activity in each frequency band. The rightmost column gives percentage time suppression (Suppr), the Muscle amplitude in $\mu$V pp, the Line frequency amplitude in $\mu$V pp, and the electrode impedance in kohms. Also shown at the bottom are the above-mentioned bandwidth corrected frequency range values. For operator information, the uncorrected values are also shown.

In FIG. 7b there is shown the skew and, in square brackets, the kurtosis. Otherwise the display is the same except there is no $\mu$V pp column and the $\mu$V rms bandwidth uncorrected figures are omitted from the bottom half.

Figure 5:
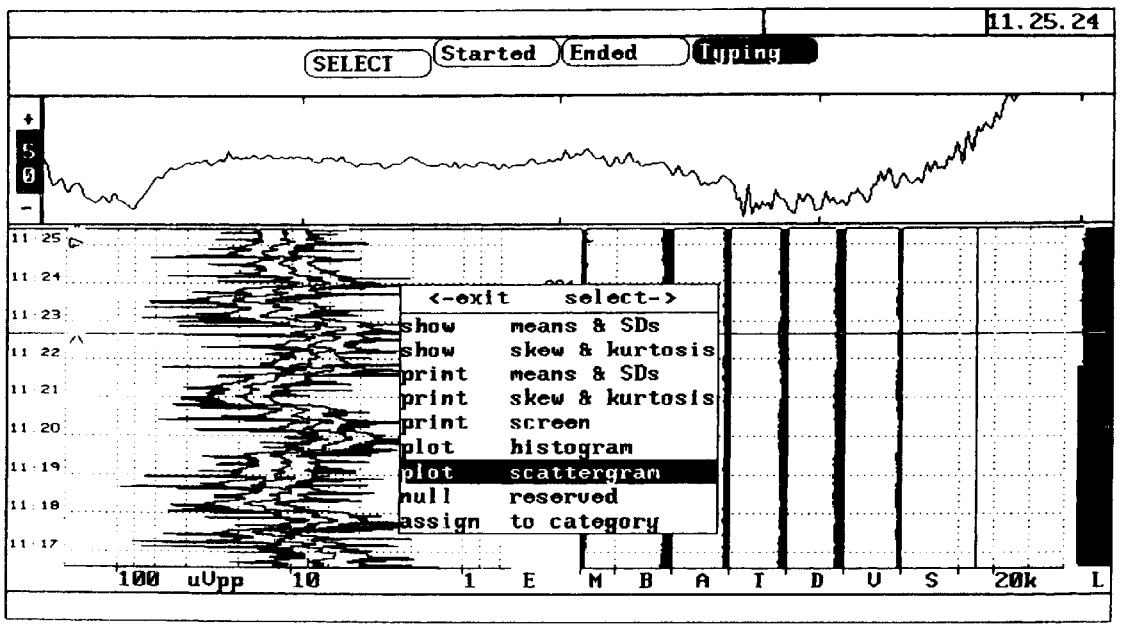
FIG. 5 shows a screen menu.
Figure 8:
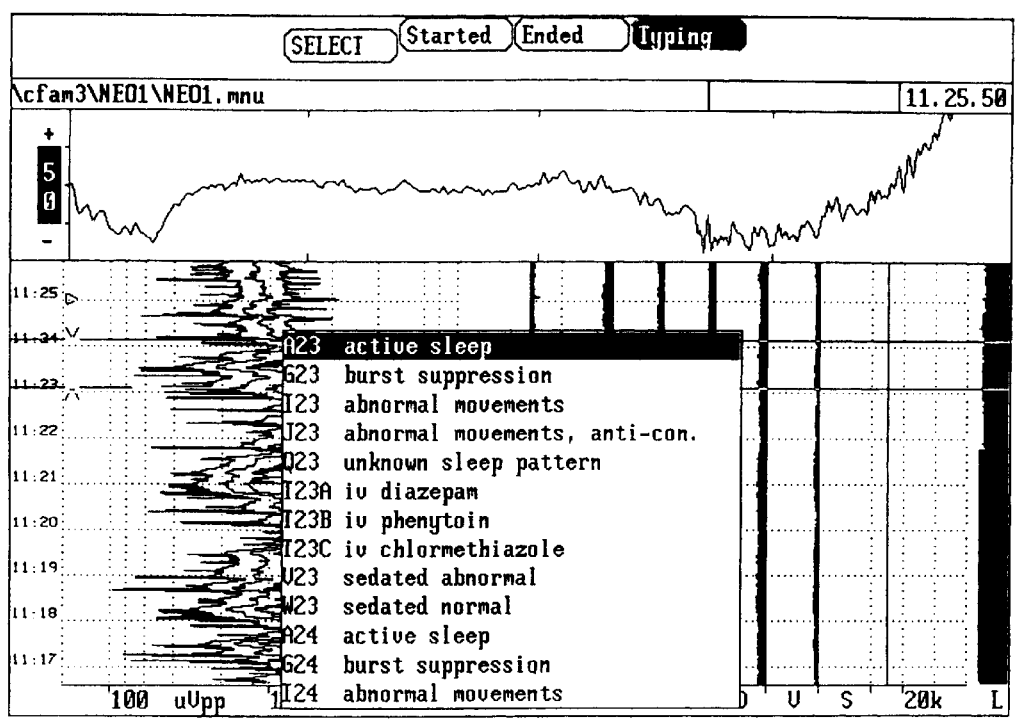
FIG. 8 shows a menu display.

The above two displays are selected from a screen menu as shown in FIG. 5. The user can also select to show histograms comparing, over a selected time interval, the distribution of one or more of the measures listed in the table above. Scattergrams of pairs of variables can also be selected. The final item on the menu, assign to category, calls up a menu of data categories, designed by the user, into one of which the user may elect to place a record of the statistics of the selected (bracketed) section of the record. This is similar to CFAM3a except that CFAM3a applied only to Zed transform classifiers. This menu is shown in FIG. 8.

In this new system, we employ a neural network, preferably programmed into the additional DSP board 12 (for a simple network it may be programmed in to the second DSP chip on board 11, time sharing with the processing of evoked potentials) and utilise multi-dimensional classification and displays. Thus, one can take as an example of a 2-dimensional system a classifier that might be state of awareness (e.g. from awake-crying, awake-handled and so on) versus age. In general, the categories used are defined by a plurality of category items. In the preferred embodiment the user defines categories in code form; e.g. A23=active sleep at 23 weeks (2-dimensional), T23A =23 week child having an infusion (T) of type A (diazem) (3-dimensional). Thus one in effect inputs a coordinate data set or vector defining coordinates in multi-dimensional space to represent the condition or category of the selected section of a patient's record. A section of a record will be placed in only one category, unless the designer deliberately defines sets of categories that may properly be dealt with by two or more classifier systems or unless the designer wishes to train the system on overlapping categories.

Generally there can be n (>1) coordinates in n-dimensional space. That space is defined by the user, as will be described.

There are also extensive means in the software to create new data categories by transferring data from old ones.

Figure 6:
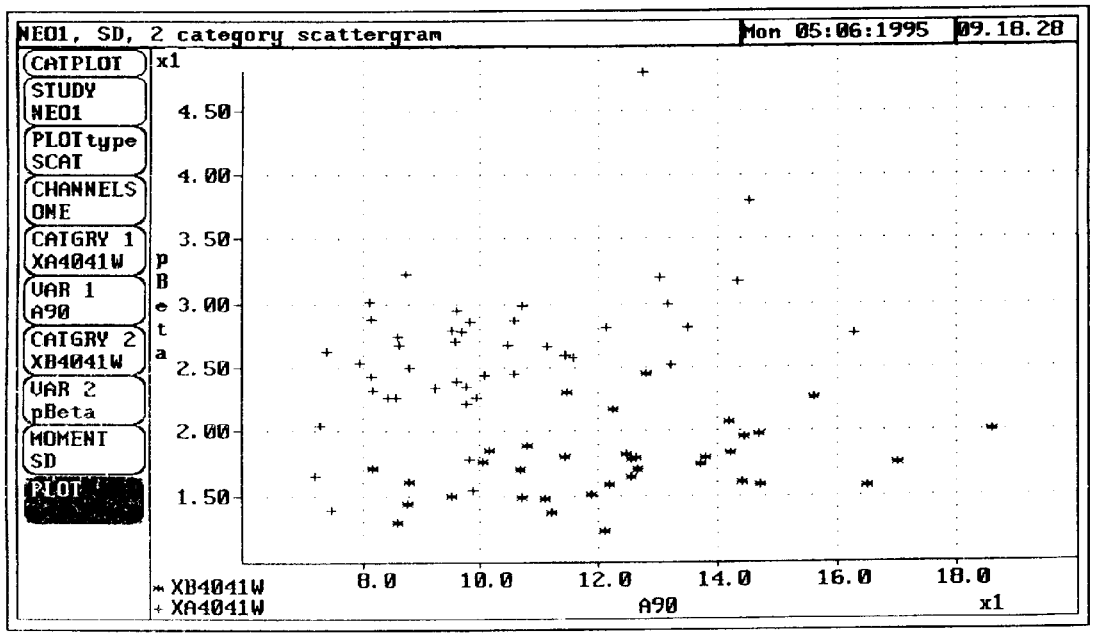
FIG. 6 shows a plot of statistical data.

There are also means for graphically displaying the values of mean, standard deviation, skew and kurtosis, of variables between categories by means of histograms and scattergrams to enable the user to assess relationships between variables and differences between categories. An example of such a plot is given in FIG. 6. The example is from a set of categories originating from a single channel recording and compares standard deviation data from two categories on a scatter plot of percent beta against 90th centile of amplitude distribution. It can be seen that the data from the two categories forms two distinct data groups indicating that the standard deviation of percent beta is, in this example, a good discriminator between the two groups.

Figure 9A:
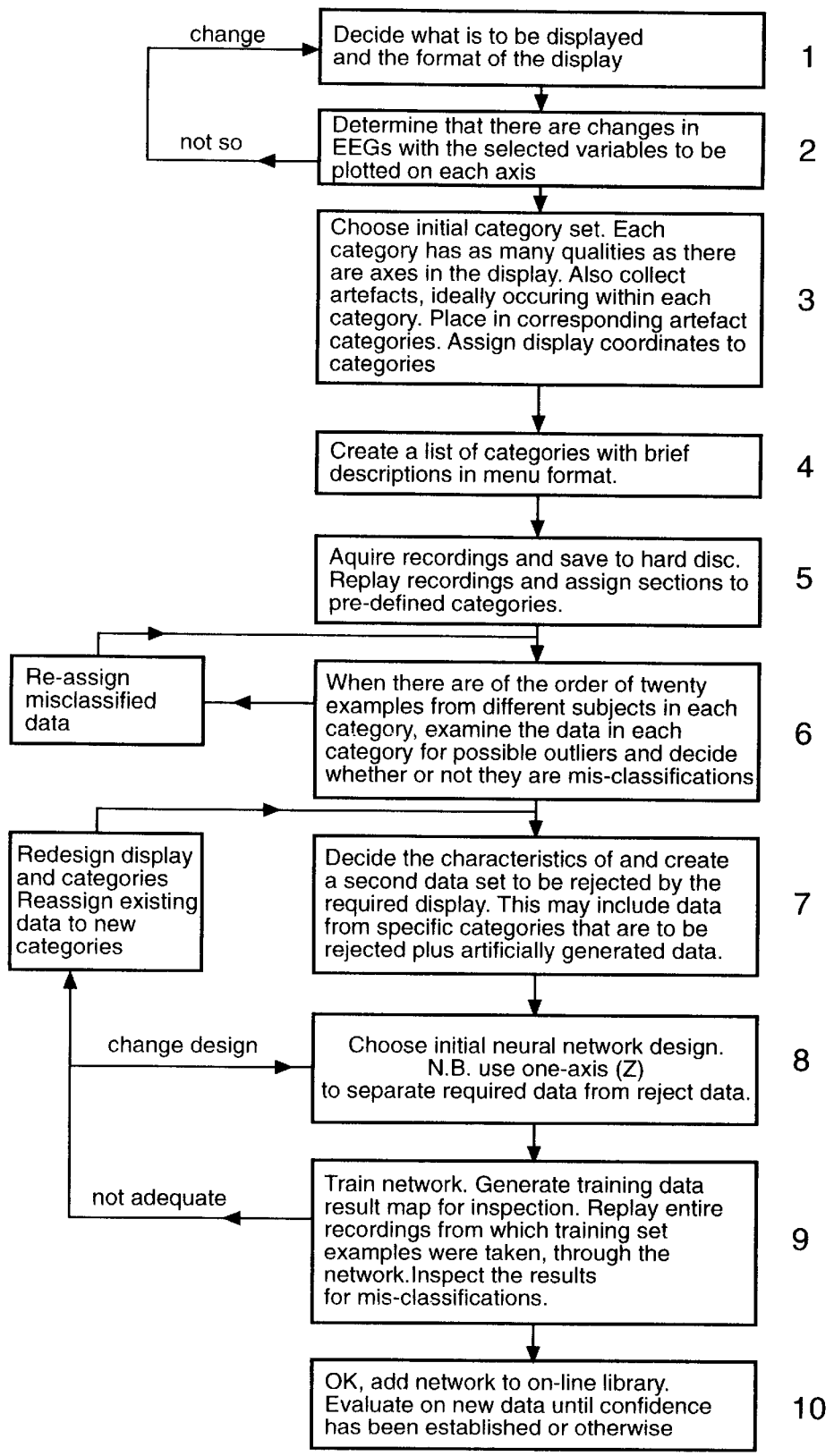
FIGS. 9a and 9b are flow charts.
Figure 9B:
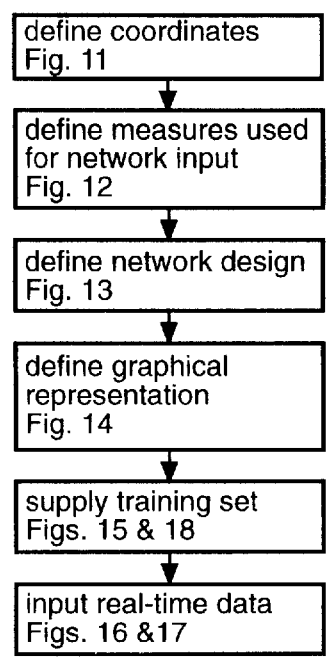

FIGS. 9a & 9b are flow charts showing the general organisation of the system and how it is used.

Block 1 in FIG. 9a represents the initial stage of the research by the user who has to consider the data that he wishes to be analysed and thus makes an initial assumption as to which categories he is going to place the data in and what sort of map or coordinate arrangement he desires to display those categories.

Block 2 represents his research to ensure that the parameters that he has chosen to define his categories are indeed parameters that change in EEGs. Examples are given later, such as awareness, age and so on and of course subcategories of those categories.

Block 3 represents a choice of the initial category set, bearing in mind that each category is n-dimensional, i.e. there are as many items or qualities as there are axes in the display. In the present example we shall consider a three axis display but even more axes are of course possible. Thus he may choose for his X, Y plane the qualities of awareness and age and in the third plane allocate coordinates for qualities such as artefacts, rejected data and perhaps other properties such as barbiturate level. With reference to artefacts, it must be bourne in mind that EEGs can contain extraneous disturbances and, when these occur, the user should define a category into which to put them. Whilst they will have a category in the X and Y plane they will need a specific coordinate value on the Z axis.

Block 4 represents the creation of the full menu of categories within the software of the machine, as was described with reference to FIG. 8.

Block 5 represents the acquisition of recordings from patients and their storage on hard disk followed by their replay in order to assign sections of those recordings to the predefined categories.

Block 6 represents the situation of having accumulated a plurality of sets of data relating to the assigned sections and then carrying out the inspection process illustrated in the Tables shown below to discover outliers. A decision has to then be made as to how to reassign these outliers on the basis that they may well constitute mis-classified data. Block 7 represents the generation of a further data set to be included within the training set and which is specifically designed to be rejected by the main X and Y display plane. A specific Z coordinate will be allocated to this data set so that it forms a reject layer in the three dimensional space defined by the user. This set can be supplemented by artificially generated data.

One then proceeds into the processing defined by FIGS. 11 to 14 which involves choosing an initial form of neural network design, bearing in mind that the Z axis is utilised to separate required data (in the main X Y plane) from reject and other data.

Block 9 corresponds to the process which will be described in relation to FIG. 15 and it involves training the network with the training data set including the statistical data of the sets being supplied as input data and the classification or category qualities as target output data. This generates a training data result map for inspection. This inspection can lead to redesign, for example because the results show misclassifications. One could initially step back a block to change the neural network design and/or go back to redesign the display and/or the categories, the latter involving reassigning the existing training data to these new categories. The process can then be repeated until one reaches the final block where one has decided that the neural network is operating correctly and its parameters are then stored as an on-line library. New data can then be evaluated in real time and of course those results can also be used to measure the success of the result. If one is still not satisfied the system can be adjusted as before.

The set of routines in the computer for carrying out blocks 8 to 10 are shown in FIG. 9b and are described in more detail below.

Having described the system in general, we proceed with details of the preferred embodiment, dealing first with the process of Block 6.

Tests for data homogeneity

A number of statistical tests are made of the data within each category to pick up statistical outliers.

For example, the following Table shows the content of the relevant screen display.
TITLE STUDY NEO1 INCLUDE DATA ONLY ITEM SKEW[KURTOSIS] SEs FROM CLASS MEANS Variables log: Amin,A10,Amean,A90, Amax, Awidths, Askew %Suppr,pVLF, pDelta, pTheta, pAlpha, pBeta

| CLASS-chan-item | | −2.6< | | |2.6| | | >2.6 | |
|---|---|---|---|---|---|---|---|---|
| DATA | total | log | % | log | % | log | % |
| XA2829W.ST1-1-000 | 61 | 0[0] | 2[3] | 3[7] | 4[3] | 4[0] | 0[0] |
| XA2829W.ST1-1-001 | 61 | 0[1] | 2[3] | 6[6] | 4[3] | 1[0] | 0[0] |
| XA2829W.ST1-1-002 | 94 | 0[1] | 2[3] | 7[6] | 4[3] | 0[0] | 0[0] |
| XA2829W.ST1-1-003 | 105 | 0[0] | 2[3] | 7[7] | 3[2] | 0[0] | 1[1] |
| XA2829W.ST1-1-004 | 30 | 0[0] | 2[3] | 7[7] | 4[3] | 0[0] | 0[0] |

-continued

| CLASS-chan-item | | −2.6< | | |2.6| | | >2.6 | |
|---|---|---|---|---|---|---|---|---|
| DATA | total | log | % | log | % | log | % |
| XA2829W.ST1-1-005 | 40 | 0[0] | 2[4] | 7[7] | 4[2] | 0[0] | 0[0] |
| XA2829W-ST1-1-006 | 89 | 0[1] | 1[4] | 7[6] | 5[2] | 0[0] | 0[0] |
| XA2829W.ST1-1-007 | 83 | 0[0] | 2[3] | 7[7] | 4[3] | 0[0] | 0[0] |
| XA2829W.ST1-1-008 | 31 | 0[0] | 2[3] | 7[7] | 4[3] | 0[0] | 0[0] |
| XA2829W.ST1-1-009 | 99 | 0[0] | 2[3] | 7[7] | 4[2] | 0[0] | 0[1] |

There are 7 amplitude measures in the log row and 6 percentage values.

The 6 rightmost colums are in three groups headed −2.6<, |2.6| and >2.6. These refer to standard errors from sample means. Each group is of two columns headed log and % respectively. The left hand side lists the individual items of which each line refers to the statistics of a single bracketed section. The first represents an item previosly place in a category defined within the software as XA2829W. This is item 000 and contains a total of 61 2 second epochs.. There are 0 (log) amplitude measures whose skew and [kurtosis] are 2.6<SEs (Standard Errors) from the mean of all the examples in category XA2829W and there are 2 skews and 3 kurtosis percentage measures which are −2.6<SEs from the category mean.

In this display, within a category the skews and kurtosis measurements have distributions with their own mean and variance for each variable. Therefore, each data sample within the category can be compared with the category mean values to see how many variables are within given standard error ranges of the means. To detect an outlier we look, within a category, for an example where the distribution of counts differs greatly from the rest of the group. There are none such in the example given, other than perhaps the first in view of its count of 4 skew values >2.6SEs from the mean, in contrast to the counts from other data sections. If it is decided that an item is in the wrong category, it can be reassigned. However, if it is an outlier which is not to appear in the main X, Y plane, it is given a Z coordinate other than 0 (the main X, Y plane). Thus, such an item can be reclassified by giving it a non-zero third dimension so that it would appear in the user space in a plane different from that of the other measures.

The following table shows another such example;
TITLE STUDY NEO1 INCLUDE DATA ONLY ITEM MEAN SEs FROM CLASS MEANS Variables log: Amin, A10, Amean,A90, Amax, Awidths, Askew %Suppr, pVLF, pDelta, pTheta, pAlpha, pBeta

| CLASS-chan-item | | −2.58< | |2.58| | >2.58 |
|---|---|---|---|---|
| DATA | total | log[%] | log[%] | log[%] |
| XA2829W.ST1-1-000 | 61 | 5[1] | 2[2] | 0[2] |
| XA2829W.ST1-1-001 | 61 | 5[0] | 2[5] | 0[0] |
| XA2829W.ST1-1-002 | 94 | 0[1] | 7[1] | 0[3] |
| XA2829W.ST1-1-003 | 105 | 2[2] | 5[0] | 0[3] |
| XA2829W.ST1-1-004 | 30 | 0[0] | 6[6] | 1[0] |
| XA2829W.ST1-1-006 | 89 | 0[2] | 7[3] | 0[0] |
| XA2829W.ST1-1-008 | 31 | 0[1] | 7[4] | 0[0] |
| XA2829W.ST1-1-009 | 99 | 0[2] | 2[3] | 5[0] |
| XA2829W.ST1-1-010 | 60 | 0[2] | 6[3] | 1[0] |

In this table, within a category, for each variable The software is comparing means with class means. The total variables in log amplitude and, in brackets, percent frequency are counted separately. Again we look for substantial differences in counts from the average pattern of counts. In this example we may suspect the first two items to be possible outliers.

The data in each category may be transferred to spread sheet programs as required by the user.

Data processing as defined by this embodiment

The aforementioned data were prepared for users of the CFAM2 to perform further data analysis by means of statistical software packages commonly available and which may be connected to this software. These may contain discriminant functions to compare and differentiate between categories. For example the statistical data in each category could be combined by means of a Zed transform and comparisons thereby made between categories. A variety of such applications have been described in patents.

However it has been found by the inventor that a class of signal processing commonly referred to as a neural network provides far better discrimination between data groups and has the specific ability, which is the feature of this embodiment, to be trained to define single outputs which may scaled in a manner defined by the user to suit his or her specific application. Each single output may then, if required, be treated as defining a deflection along an X, Y or Z axis, so enabling one, two or three dimensional graphs to be generated. Further any such output may also be shown varying along a time axis.

Neural networks vary in complexity according to the difficulty of the task required. A simple network may consist of a single element in which weights are applied (multiplied by) to each input variable, with the results summed to provide a single output. A complex network may consist of many such sets of weights in a single layer, with an output for each set being supplied as input to another layer which has its own set of weights and so on until the desired scaled output is achieved. Networks may be trained by adapting weights to minimise the errors in the outputs. The cycle of trial and adaptation may be repeated a very large number of times, for example 10,000, before a satisfactory solution is reached.

A number of types of neural network may be used. One example of neural network found to be efficacious for this data is that known as the Feedforward Network with adaptation being controlled by the Conjugate Gradient method with Annealing and which is trained by Back Propagation of Errors. These terms may be found explained in detail in "practical Neural Network Recipes in C++" by Timothy Masters., ISBN 0-12-479040-2. A simplification may be made for a single layer neuron whereby the output does not have to be found by adaptation but may be computed directly by linear regression using Singular Value Decomposition, again refered to in T Masters.

Figure 10:
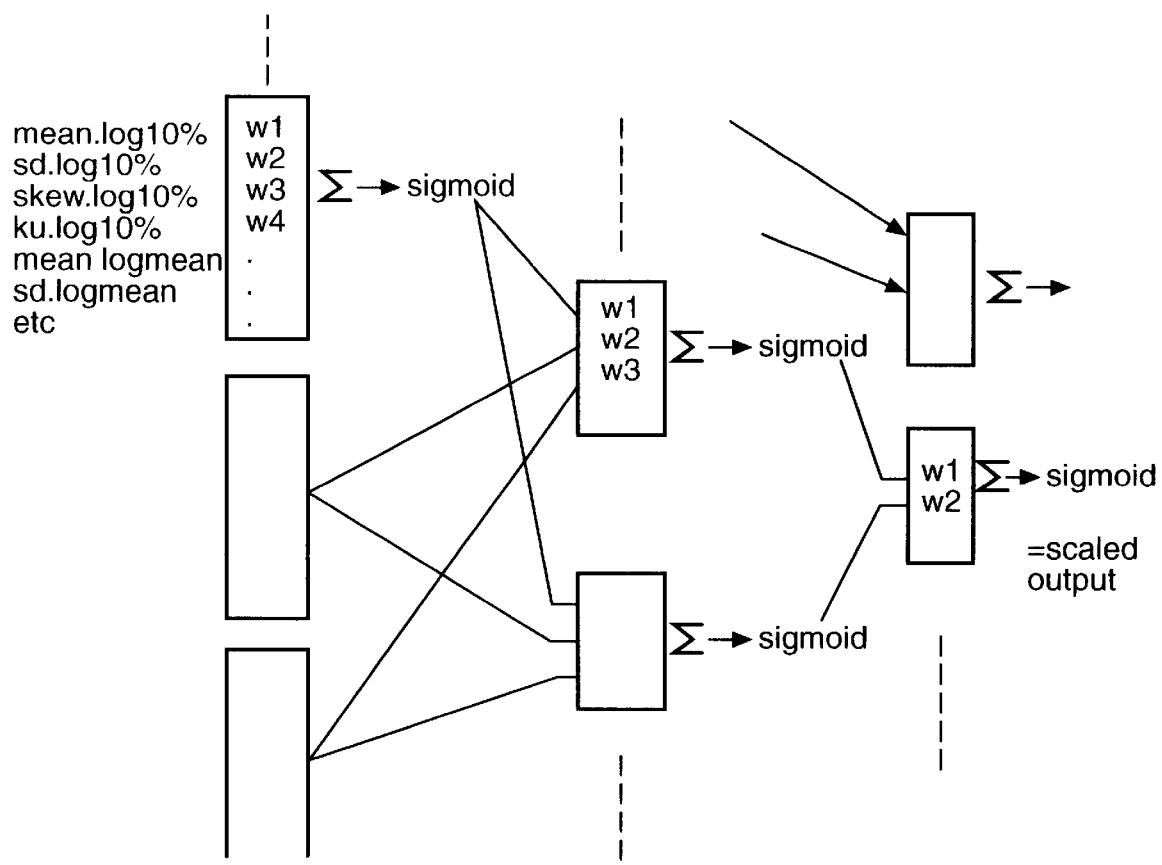
FIG. 10 shows a diagram of neural network processing.

FIG. 10 shows the pattern of connection of elements in a neural network of the type described. Statistical outputs produced from a section of EEG are multiplied by input weights in the first layer. The outputs are summed and then constrained between values 0 and 1.0 by means of a sigmoidal amplitude compression function. There may be many such sets of weights in the first layer. The outputs from the first layer are then input to a further layer consisting of a plurality of elements each with its own set of weights. The outputs from this layer, in the illustration, are then input into a final layer having at least two elements or neurons which output the desired at least two scaled data values. The preferred embodiment being described uses three outputs for three dimensions X, Y and Z.

The software associated with the neural network requires user input according to the following verbal flowchart:

1. DEFINE COORDINATES FOR CLASSES

Having acquired a data set the user is required by the software to define coordinates for his classes of data. An example of the users input is given in FIG. 11. Each data row contains the data category (e.g. XA2828W), its coordinates on X, Y and Z axes (e.g. 030,050,000—note that the third axis is not used here, i.e. is 000) the total number of samples in the category (e.g. <0064>), and a description of that category. It is useful for the coordinates to be separated by large intervals to enable one to introduce non-linearities in the output scale if so desired. The software generates this display with zero X, Y and Z coordinates and the user merely alters the coordinates.

2. DEFINE MEASURES TO BE USED AS NETWORK INPUTS

The user is then required by the software to define which data measures are to be included as inputs to the network, as in FIG. 12. The variables are grouped as means, standard deviations, skews and kurtoses, each of which may be included or excluded as a whole, followed by the individual variable. For example Lmin followed by a zero means that the minimum level of line interference (50/60 Hz) is not to be used as an input (i.e. 0=exlude and 1=include).

3. DEFINE NETWORK

The user also defines the design of the neural network to be used as in FIG. 13. Contrary to some usage, we shall call the input layer a first hidden layer so that the example of FIG. 10 has two hidden layers. In this example there are defined by the user 80 input variables, 25 sets of weights in the first layer, 25 in the second and 2 in the output layer. NNET_B defines that the outputs relate to respective axes. This line can be toggled to give different types of network and organisation. For example, NNET_A would mean a separate axis for each data category, i.e. a 0 or 1 value per category, giving a network of p output neurons for p categories. In that case the multi-dimensional space shows only the nearest category, and would maintain a count of samples at each coordinate concerned.

The line AXIS XY is a message indicating that the network as defined will have two outputs, one for each axis. We have found that using NNET_B, training all axes together, is more powerful in classifying data than trying to train the axes individually.

When measuring the effectiveness of training we have found that two measures are especially useful. Firstly the average error of the output from that desired over all of the training sets, this being used to control the direction of adaptation, and another which simply acts as an indicator which will display on the screen and which is the total percentage of samples falling within a defined area about the required value of the scale. Typically this area would have dimensions of 50% of the interval between the desired scale value of a category and that of the adjacent categories. The term T_RANGE 05 in FIG. 13 defines that the area to extend 50% between graduations as there are in this example 10 units between the main coordinate graduations. When the display of T_RANGE shows a significant slowing of the rate of increase of "correct" classifications, the user can see that the time is approaching when training can cease.

4. DEFINE GRAPHICAL REPRESENTATION

The user also defines a graphical representation of the data. In FIG. 14 there is shown a user-entered text list which controls the plot required, one example of the plot being shown in FIG. 15. The set of XYINCL coordinates forms an optional dotted line around the data display. DISPLAYS 1, XY defines that there is only one plot displayed on the screen and that it has XY axes. YMIN, YMAX, XMIN, XMAX define the limits of those axes in terms of the coordinate system defined by the user. XLABEL and YLABEL are X and Y axis labels. The LTX and LTY items are labelling data; e.g. LTX 20, 27 means label the x axis at coordinate 20 with the text '27'. LTY60, Quiet means label the coordinate 60 on the Y axis with the text 'Quiet.'

5. TRAINING

Data values already obtained for the sets of data classified as at 1. above are now recovered from disc and applied to the network s as training data. The weights of the network automatically adjust to fit the sets, with the result that compromises will give a proportion of the data sets coordinates in the defined space which do not fit exactly the predefined coordinates. These "errors" mean that similar sets of data will cluster around the corresponding coordinates.

Figure 15:
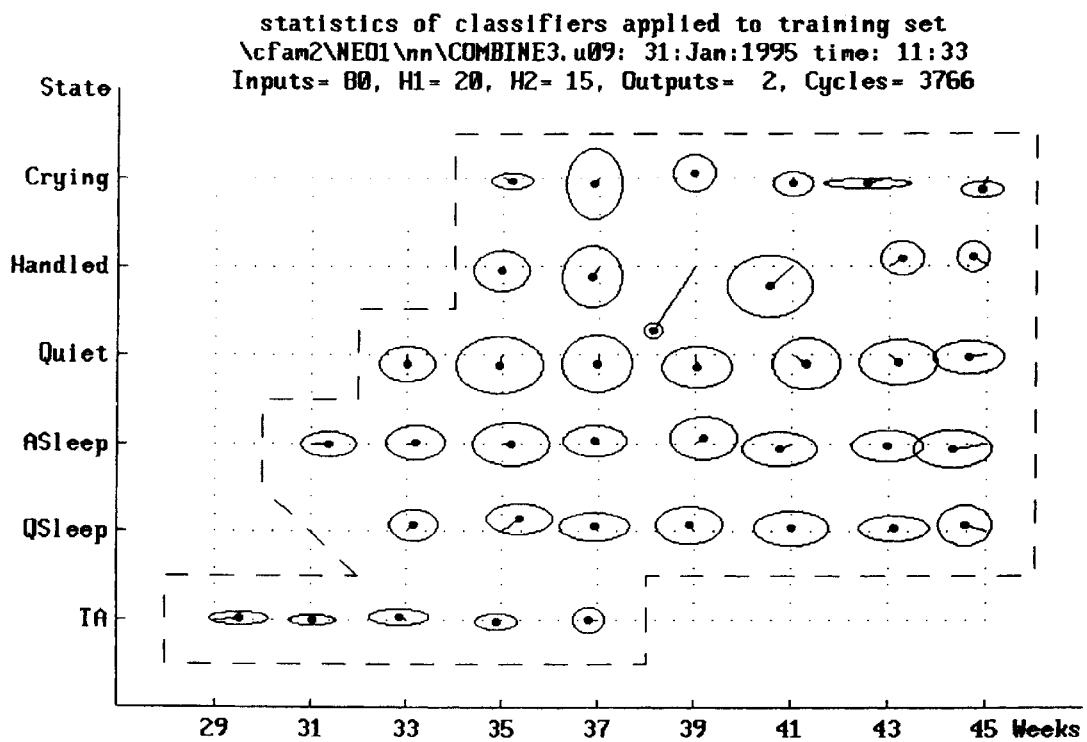
FIG. 15 shows a plot of training data applied to the network.

FIG. 15 shows one form of display produced by the above list when a trained neural network is applied to a training data set or a test data set acquired from neonates of various age groups. On the vertical axis is shown the state of awareness of the neonate. On the horizontal axis is shown the gestational age of the neonate at the time of recording. The network has been trained to place the data on the cross points of the graticules, each cross point being a desired coordinate for a particular category. The data distribution of the training data in each category is shown by the black dot, being the mean of the distribution, with an ellipse at one standard deviation of the error. Where the mean is not at the desired graticule point a line is drawn from it to that point.

Clearly, if the neural network is now placed on-line during actual recording from a neonate, with the requisite statistical input being computed in one minute epochs say, and a dot is placed at the coordinates produced from each successive minute then, over a period of time, a distribution will be obtained of the varying states of awareness of the neonate, ideally with the centre of the distribution along the horizontal (age) axis being at that neonate's gestational age. Deviation of the coordinate from the expected age, giving an estimated developmental age some weeks less, may be an indicator of brain damage.

Figure 16:
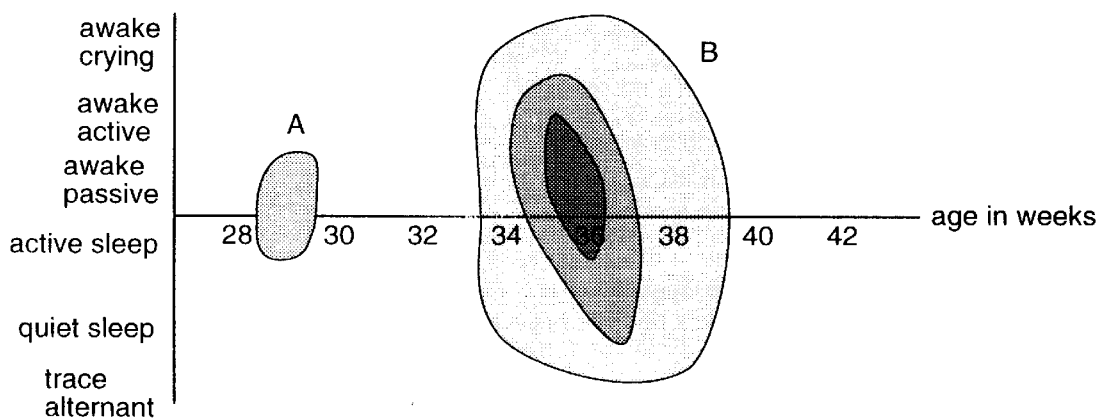
FIG. 16 shows a contour plot of data from a single recording processed by the network.

Accordingly there is a software routine for automatically displaying such a data classification, such as in FIG. 16. As data arrives (it can be in real time) from a patient, each one minute epoch of data can be processed by the neural network to produce the outputs in X and Y ( and perhaps more) which will give a specific position in the 2-dimensional space provided and display as a dot. When sufficient measures have been accumulated, the dot distribution is transformed to a contour plot as shown in FIG. 16, where the darkest areas coincide with the greatest density of dots.

Trend limits can be set by the user. Normally the sections of records chosen as the training set will be chosen as having little or no discernible trend. However, when applied to new data, trends may emerge which are not in the training set. The user can thus set trend limits to determine when the network can or cannot be properly applied.

Figure 17:
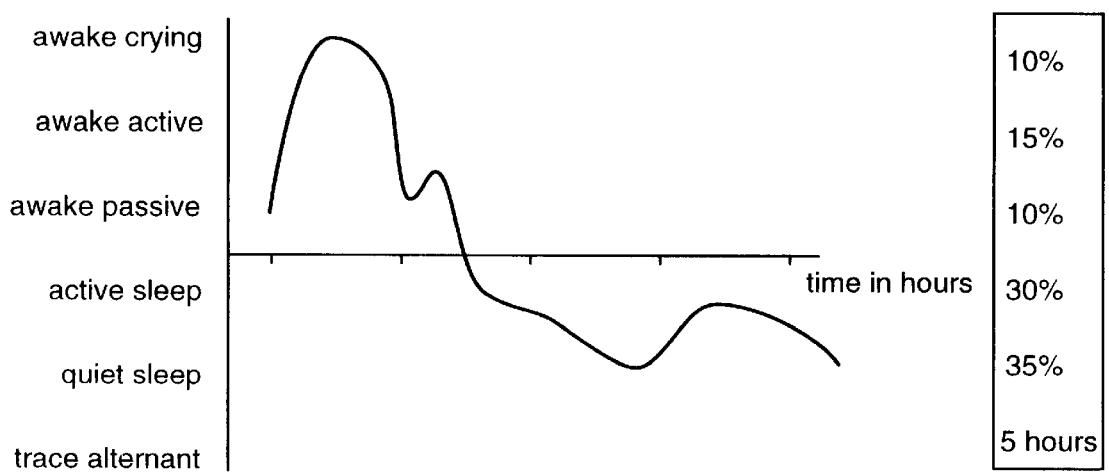
FIG. 17 shows a plot of the data of FIG. 16 versus time.

A routine is also provided for plotting state of awareness (Y) along a time axis to show if the neonate is obtaining an adequate pattern of sleep or is being disturbed too often for example. The type of plot produced for this particular application is given in FIG. 17. This may be placed on the same display as the plot in FIG. 15 or 16. The plot positions are controlled by instructions which are a development of those shown in FIG. 14 and written by the user. On the right of the plot is given the percentage time that the neonate has spent in the various states of awareness over the previous 5 hours.

The method of transforming input data by means of a neural network or networks to axes on a graphical plot is by no means limited to this example of premature neonates. It is intended that the user shall be able to define whatever axes he requires, for example senility, severity of paroxysmal activity (seizures), depth of coma, prediction of outcome after head injury to name but a few. Provided that the user defines suitable categories and acquires an adequate amount of data in each category then, if such data does contain sufficient discriminative information, he/she should be able to define whatever graphical display is useful for his/her application and train the network to produce the appropriate X, Y, Z and even further values. Incidentally, the Z dimension might be used to capture values that represent errors or a property such as sex or drug dose.

A further step to improve the accuracy of the display may be defined in cases such as the neonate data illustrated. Here data along the gestational age axis has been collected into age groups for the purpose of defining categories. However such data originates as a continuous variable. Therefore, having established the complexity of neural network required to obtain a satisfactory result, this particular input may then revert to a continuous distribution, having a required continuous distribution of axis value outputs. The network may then be retrained.

Assistance with placing categories at relevant coordinates

Initially the user may not know precisely the positional relationship to use between categories on his desired plot. Some guidance can be obtained by obtaining category means of statistics, scaling all data distributions for each variable in common across categories so that they all lie within +−1.0, and then measuring the Euclidian distances between each category. Inspection then shows which categories are closest to each other. If this is not adequate, a Kohonen self-organising neural network may be added so that it can be fed training data to place that data on an appropriately dimensioned map. Data in each category should then cluster on this map. Examination of this data, when it has ceased to adapt significantly, together with category information, can give an indication of which data categories should be adjacent. From this an appropriate target layout can be determined. However it is a weak classifier and non-adjacent categories or overlapping categories in a Kohonen map can frequently be made adjacent and separate by the Feedforward neural network described. The Kohonen output may also be stopped from adapting at a suitable point and be used as the first layer of the main network. In the preferred embodiment we would instead train the main network afresh.

Testing of solution

The traditional method of testing the efficacy of a neural network solution is to divide the data into a training set and a test set. Several selections of training and test data may be made to determine the likely accuracy of the solution. Where input data are transformed to values along multiple axes as here, estimating the statistical significance of separation between data classes in the multi-dimensional space thus defined can now be performed by relatively simple statistical tests. However when selecting tests it should be remembered that the data distributions ideally should be even along each interval of the axes unless distortions can be tolerated which will tend to cluster data in each category at the central coordinates for that category. Such tests may be found in conventional statistical software packages to which the results of this analysis may be transferred.

Variables used as inputs to the neural networks

In the example of the neonate data, the system has computed means, standard deviations, skews and kurtoses of individual variables to be used as inputs to the neural networks. Where these do not contain sufficient information to enable satisfactory scales to be generated, other measures may be added, such as correlations between the variables both within a single channel and across several channels.

Further, where the record characteristic one is trying to recognise and place on a scale is short in duration, such as may occur for example in a brief episode of paroxysmal brain activity, or has a rapid transient such as in response to a bolus of drug administered intravenously, such statistical measures requiring a sufficiency of measures to enable means and other moments to be calculated with some accuracy may not be adequate.

Here we may choose to replace or supplement these with trend statistics of variables, for example Triggs Tracking Factor (1964, "Monitoring a forecasting system", operat. Res. Quart., 15, 271–274) and later refinements and methods for example those reviewed by Endresen and Hill (1977, "The present state of trend detection and prediction in patient monitoring", Intens. Care. Med., 3, 15–26).

Where data acquired in epochs, such as the 2 second epochs, does not provide adequate detail of a trend, or cannot indicate the presence of specific waveforms for example, then a more continuous input of processed data may be necessary.

Hardware Neural Network

Where a neural network does not consist of many elements and few such networks performing different classifying tasks are operating in parallel, then the networks may be simulated/calculated using a suitable digital signal processor. In the CFAM3a for example there is a spare Motorola DSP56002 digital signal processor which may be used for this purpose.

In the neonate example illustrated in FIG. 15, such networks may be applied conveniently in one minute successive epochs on accumulated statistical data in each epoch. However we may choose to apply the networks to the last minute of data every 2 seconds, for example adding an arrow to the plot of FIG. 16 to indicate direction and speed of a trend from the present coordinates. This may provide a heavy computing load if the number of scaling tasks operating in parallel is large and the neural networks for each are complex. Indeed if the input data requirements for the scale generation task are such as to require continuous, as opposed to epoch, processed data, then one can either use multiple parallel DSPs and/or special function neural network chips as are available commercially. In the preferred embodiment all such chips are intended to be on the special function printed circuit board 12 plugged into an IBM ISA backplane, with a link from the existing digital signal processors.

Advantage of the Embodiment

Figure 18:
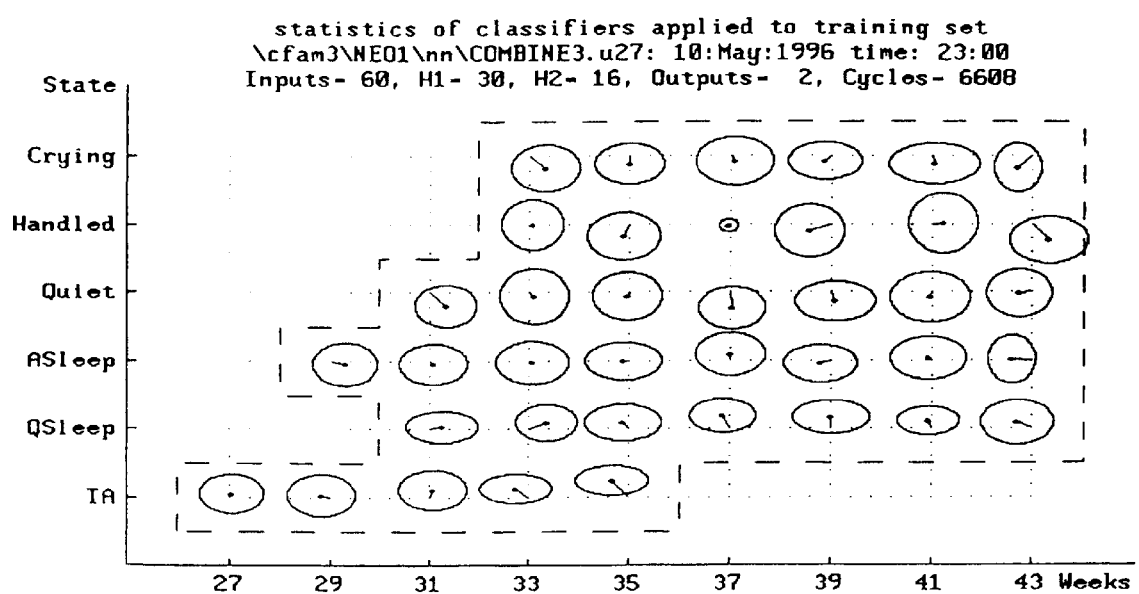
FIG. 18 shows a plot of training data with a modified error assessment.

Data category classification systems based upon the recognition of single categories, such as may be obtained for example by the Z transform, use different scaling of input variables for each category and cannot readily be made to output those categories as continues distributions along common axes. The new method described herein permits categories to be be placed at specific coordinates within a graphical display with common axes for all categories. Such variations of individual variable scaling as may be implemented automatically within the neural network are hidden from the user. Training a single neural network to produce multiple axis outputs has greater powers of resolution in separating categories than training separate networks for each axis. In the data of FIGS. 15 and 18, using classes on the described XY plot (25-15-2) gave 98.5% success (within the +−T_RANGE of category coordinates). If the same data is used to train a network only on the awareness axis (all ages combined), only 81% correct classifications could be obtained (with layers with neuron counts of 25-15-1). The same data used to train just age (all states of awareness combined)) gave 54% success (25-15-1).

Alternative back propagation error derivation

A particular difficulty of a neural network trained to classify data in category groups along an axis is that it attempts to place all data in a category at the central coordinate for that category. In doing this it will generate a form of distortion of the scaling on the axes between adjacent categories. The effect of this is that data occurring between two particular categories may be placed erroneously in a completely different portion of the display, in the region between two other categories. To avoid this distortion, it is possible to use a modified error term. Instead of the error term being measured from the desired central coordinate (which gives the result of FIG. 15), the term is, in this modification, measured from a boundary surrounding the central coordinate. Thus an area is chosen around the defined coordinate which is taken by the network during training as being error free. The furthest extent of this boundary would normally be half way between category coordinates, for example the T_RANGE term in FIG. 13.

FIG. 18 illustrates the same data set as in FIG. 15, but trained to a boundary of 0.9*T_RANGE, i.e. 45% of distance between centres. The preferred range would be 0.8 to 1 (0.4 to 0.5 of the distance mid-way between neighbours) or 0.8 to 0.95, but a range as low as 0.5 may suffice (0.25 of mid-way distance). Data falling within the boundary is deemed to have zero error. A particular advantage of this approach is that, in practice, equal numbers of data are not available in each class. Normally in the learning process, greatest weight is generated by those classes having the largest number of examples. However once a sample falls within the boundary, it ceases to influence the adaptation. In consequence as training continues the number of items in each category contributing to the error term tends to equalise. A single input example for each category, equal to the category mean, can have its error term calculated from the desired category central coordinates. This pulls the centre of the distribution towards the desired coordinates. In FIG. 18 the item at coordinate Handled—37 weeks consists of a single training example.

In practice a number of, or variable, boundaries may be used. For example, each input example may have its boundary set according to, or as function of, its deviation from the category mean, with for example 2 standard deviations being made equal to 0.7*T_RANGE for that example. In a further development, a negative error can be applied within the boundary to drag such an item towards its boundary.

Error assessment

Some input data will inevitably be sufficiently different from the training set to produce errors. Accordingly it is necessary to apply some checks. For example we can, for each category, keep the statistics (mean and standard deviation, and/or maxima and minima) from the training set of all of the outputs from the first layer. On new data, when the network has determined a category, we can then compare the first layer outputs with the norm for that category. If the deviation from the norm exceeds a limit supplied by the user, the network output is considered unreliable and discarded. A further layer of protection compares the data input to the network with norms for the category identified by the network in the manner indicated in the above Tables. Again limits are set by the user. In general these user supplied limits are derived from replaying records and adjusted until the user is satisfied of appropriate performance.

The possibility of the network producing an erroneous output, onto a 2-dimensional map for example, from data not typical of the training set can be reduced by including an extra dimension or axis. The network is then trained so that certain classes of data which is intended to be shown on the map is either limited between particular coordinates on the further axis (axis Z in the above example) or below a given coordinate on that axis. Data categories which are not to appear on the main map can be placed outside the coordinates or above the the given coordinate. Random data may also be generated and added to the exclusion class after testing that is not within a given number of standard deviations from the class mean. Thus, the data we require to be shown on the map is given one coordinate on the extra axis (Z), say 20. The data we do not wish to appear is given other Z coordinates, say >30. The network is then trained to produce 3 axes. We then only display for practical use, the particular XY place within T_RANGE of Z coordinate 20.

Into Z>30 we would therefore place data from categories we may have acquired but do not wish to appear on our desired XY plane.

Although this discussion has concentrated upon the Feed-forward Network, fewer errors and more readily statistically tested weight outputs, may be obtained by using, at least in the input layer, a network based on Euclidean distance between weights and the input data. On occasion a better performance may be obtained by using a totally Euclidean network, and that described by Dorffner ("EuclidNet- A Multilayer Neural Network using the Euclidean Distance as Propagation Rule", Artificial Neural Networks, 2(eds) Aleksander and Taylor), 1992 Elsevier Science Publishers BV.) may be chosen.

Similarly the input layer may also be substituted by the outputs of a trained Kohonen network ("Self Organised Formation of Topologically Correct Feature Maps", T.Kohonen, 1982, Biological Cybernetics, 43,:59–69)/

Neural network training

In the preferred embodiment a novel means was adopted for calculating the error to be fed back to earlier layers for adjusting the weights.

For a layer, if o is the actual output vector (input to the next layer) and t is the target output vector, then conventionally the delta-logistic (or d-logistic or dl) is found as:

$$dl = \Sigma o_n (1-o_n)(t_n-o_n)$$

This is a single value which is then used to multiply the weights of the the previous layer to get the error outputs for that layer.

In contrast, in the preferred embodiment, dl is retained as a vector. Thus, there is calculated a dl value for each neuron. Assumme a two neuron layer, then a vector $dl_1$, $dl_2$ is computed;

$dl_1 = o_1(1-o_1)(t_1-o_1)$, and $dl_2 = o_2(1-o_2)(t_2-o_2)$

Thus if a layer has neurons with sets of weights (W11, W12,...), (W21, W22, . . . ) and so on, then in previous networks the errors of that layer would be calculated as e1=dl(W11+W21. . . ), e2=dl(W12+W22. . . ), . . . Using a vector d-logistic gives e1=$dl_1$(W11)+$dl_2$(W21) . . . , e2=$dl_1$(W12)+$dl_2$(W22) . . .

It is claimed:

1. Apparatus for electroencephalographic (EEG) patient monitoring, the apparatus comprising:

input circuitry for receiving signals from patient measurements, including signals representative of patients' brain waves, the input means including amplifier means and signal processing means for amplitude and spectral analysis of the signals to provide for each of a plurality of epochs of the signals a set of signals including signals representative of a plurality of amplitude and frequency properties of the brain waves;

means for applying statistical processing to the set of signals to derive therefrom a set of values representative of the brain waves in the associated signal epoch;

input means for defining for each of a plurality of said epochs n where n is at least equal to 2 classifying values so that each epoch is categorised by n values and wherein of those n values there are x where x is greater than which are multivalued to define an x-dimensional space;

neural network means including means defining adjustable weightings and having a training mode for deriving, from training input data comprising a plurality of said sets of values and from target outputs comprising the associated defined classifying values, output classifying values representative of patient conditions and a classifying mode for deriving from one of said sets of values n output classifying values obtained from the neural network means as conditioned by training in the training mode, the neural network means comprising:

means for calculating in said training mode weighting errors between output classifying values and the target outputs corresponding to the input data from which the output classifying values are derived;

means for defining as a substantially zero weighting error any calculated weighting error which is less than a predefined distance from the classifying value of the epoch concerned; and means for adjusting said weightings of the neural network means in dependence upon determined weighting error;

display means for displaying in x-dimensional form the x output classifying values of the neural network means; and memory means for storing data values obtained from the input circuitry.

2. Apparatus for electroencephalographic (EEG) patient monitoring of patient states, the apparatus comprising:

input circuitry for receiving signals including signals representative of brain waves of the patients;

signal processing means for amplitude and for spectral analysis of the signals to provide for each patient a set of signals, including signals representative of a plurality of amplitude and frequency properties of the brain waves;

means for applying statistical processing to each set of signals to derive therefrom respective data sets of values;

means defining an n-dimensional where n is at least equal to 2 space;

input means for defining categories for said data set by inputting coordinate sets defining coordinates in said space to categorise respective states of patients;

display means for displaying a zone containing at least a first and a second multivalued dimension of said n-dimensional space;

supervised learning neural network means having a plurality of layers, with each layer including adjustable weighting, the neural network means having:
(a) a training mode for acting upon a plurality of said sets of values obtained from respective patient measurements and from a corresponding plurality of target outputs which are defined coordinates defining the category of those patients to adjust said weightings to produce therefrom output classifying values in said space and representative of the category of the patients; and
(b) a classifying mode for deriving, from a set of said values and said adjusted weightings, output classifying coordinate values in, and for display by the input means in, said space; and memory means for storing data values obtained from the input circuitry and signal processing means.

3. Apparatus as defined in claim 2 wherein the neural network means has: means for calculating weighting errors between the outputs of a layer and target outputs corresponding to the associated input data set; means for adjusting the weightings in dependence upon any calculated weighting error; and means for defining as a zero weighting error any calculated weighting error less than an error value corresponding to a predetermined distance value which is at least 0.25 of the distance from the position in said space of said set and nearest neighbours thereof.

4. Apparatus according to claim 3 wherein said error value is a predetermined distance between 0.4 and 0.5 of said distance.

5. A method of determining EEG categories of patients, the method comprising:
obtaining a plurality of sets of training data from patient data including EEG records of a plurality of patients;
determining categories for classifying said sets, each category being defined by n where n is an integer greater than 1 classifying items;
defining an n-dimensional space in which said determined categories are represented as distinct coordinates of which at least two dimensions are multivalued;
training a neural network with n outputs, utilising said plurality of sets as input data and said defined categories as target outputs; and
applying a set of EEG data from a patient to the neural network to derive therefrom a position in said space, whereby a patient category can be assessed.

6. A method according to claim 5 wherein obtaining training data comprises:
making EEG measurements upon a plurality of patients to obtain respective patient records;
obtaining for each of a plurality of sections of said records a first set of values representing statistical relationships between amplitudes of said records;
dividing each such section into bands of different frequency ranges;
obtaining from those ranges for each section a second set of values representing statistical relationships between magnitudes in each band over the associated section; and said sets of training data comprise combinations of the first and second sets of values.

7. A method according to claim 5, and comprising effecting the step of statistical analysis on the EEG records to define outliers in respect of said categories.

8. A method according to claim 6 wherein n is greater than 2 and wherein the categories of data include a classifying item representing a coordinate in one of the dimensions of said space other than the dimensions of said at least two coordinates.

9. A method according to claim 5 wherein the neural network has a plurality of layers with each layer including adjustable weighting and the training of the neural network comprises:
calculating weighting errors between the outputs of a layer and target outputs corresponding to the associated input data set;
adjusting the weightings in dependence upon any calculated weighting error; and
defining as a zero weighting error any calculated weighting error less than an error value corresponding to a predetermined distance value which is at least 0.25 of the distance from the position in said space of said set and nearest neighbours thereof.

10. A method according to claim 5 wherein the training of the neural network comprises:
calculating weighting errors between the outputs of a layer and target outputs corresponding to the associated input data set;
adjusting the weightings in dependence upon any calculated weighting error; and
defining as a zero weighting error any calculated weighting error at a given distance from the position in said space of said set;
defining a negative error within said distance.

11. A method according to claim 5, wherein the training of the neural network comprises:
defining for each example of said input data a boundary about its target output;
calculating weighting errors in dependence upon the distances between the outputs of a layer and the boundaries corresponding to the target outputs; and
adjusting said weightings in dependence upon any calculated weighting errors.

12. A method according to claim 11, wherein the calculating step comprises calculating the weighting errors so as to generate negative errors within the boundaries, thus to tend to drag each item of input data towards its boundary.

13. Apparatus for electroencephalographic (EEG) patient monitoring of patient states, the apparatus comprising:
input circuitry for receiving from a plurality of electrodes attached to sectors of patients' heads signals representative of brain waves of the patients;
signal processing means for amplitude and for spectral analysis of the signals to provide for each patient a set of signals, including signals representative of a plurality of amplitude and frequency properties of the brain waves;
means for applying statistical processing to each set of signals to derive therefrom respective data sets of values;
means defining an n-dimensional where n is at least equal to 2 space;
input means for defining categories for said data set by inputting coordinate sets defining coordinates in said space to categorise respective states of patients;

display means for displaying a zone containing at least a first and a second substantially continuous dimension of said n-dimensional space;

supervised learning neural network means having a plurality of layers, with each layer including adjustable weighting, the neural network means having:
  (a) a training mode for acting upon a plurality of said sets of values obtained from respective patient measurements and from a corresponding plurality of target outputs which are defined coordinates defining the category of those patients to adjust said weightings to produce therefrom output classifying values in said space and representative of the category of the patients;
  (b) a classifying mode for deriving, from a set of said values and said adjusted weightings, output classifying coordinate values in, and for display by the input means in, said space; and
  (c) means for calulating a delta-logistic parameter for weighting adjustments of layers as a vector; and memory means for storing data values obtained from the input circuitry and signal processing means.

14. A method of determining EEG categories of patients, the method comprising:

the step of obtaining a plurality of sets of training data from patient data including EEG records of a plurality of patients;

the step of determining categories for classifying said sets, each category being defined by n where n is an integer greater than 2 classifying items;

the step of defining an n-dimensional space in which said determined categories are represented as distinct coordinates of which at least two coordinates are substantially continuous;

the step of training a supervised learning neural network with n outputs, utilising said plurality of sets as input data and said defined categories as target outputs, the training of the neural network comprising:

calculating weighting errors between the outputs of a layer and target outputs corresponding to the associated input data set;

adjusting the weightings in dependence upon any calculated weighting error;

defining as a zero weighting error any calculated weighting error at a predefined distance from the position in said space of said set and said given distance is a function of the standard deviation from a population mean of the associated category; and defining a negative error within said distance; and the step of applying a set of EEG data from a patient to the neural network to derive therefrom a position in said space, whereby a patient category can be assessed.

15. An apparatus for EEG patient classification from data conveyed by measurements carried out upon a patient, the measurements comprising EEG measurements of brain waves and the apparatus comprising:

input means arranged for the inputting to the apparatus of:
  (a) a plurality of sets of training data representative of measurements obtained from a plurality of patients;
  (b) categories for classifying said sets and each category being defined by n where n is an integer greater than 2 classifying items of which at least a first and a second are multivalued and a further classifying item categorises the sets into at least two types; and
  (c) a set of data obtained from measurements carried out upon a patient;

means arranged to define a category space having n-dimensions in which space said categories are represented as distinct coordinates;

means for displaying at least a portion of said space defined by dimensions corresponding to at least said first and second of said n-dimensions; and means defining a supervised learning neural network with n outputs and having:
  (a) a training mode for utilising said plurality of sets as input data and said categories as target outputs to derive a trained version of said neural network; and
  (b) a classifying mode for using the trained neural network to derive a patient category in said n-dimensional space from said set of data obtained from a patient.

16. An apparatus according to claim 15, and comprising means responsive to input data in which the further classifying item defines the presence and absence of outliers in data obtained from measurements carried out upon a patient so that the display means is able to display a portion of said space substantially free of such outliers.

* * * * *